(12) United States Patent
Werpy et al.

(10) Patent No.: US 6,545,175 B1
(45) Date of Patent: Apr. 8, 2003

(54) ESTER COMPOUNDS AND THEIR USE IN FORMING ACRYLATES

(75) Inventors: Todd A. Werpy, West Richland, WA (US); Michael A. Lilga, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/691,143

(22) Filed: Oct. 19, 2000

(51) Int. Cl.⁷ .......................... C07C 67/30; C07C 69/66
(52) U.S. Cl. .................. 560/212; 560/185; 560/211
(58) Field of Search ................. 560/211, 212, 560/185

(56) References Cited

U.S. PATENT DOCUMENTS

| 3,208,857 A | | 9/1965 | Howard et al. | |
|---|---|---|---|---|
| 3,487,101 A | | 12/1969 | Völker et al. | 260/486 |
| 4,529,816 A | | 7/1985 | DeColibus et al. | 560/212 |
| 4,617,405 A | | 10/1986 | Kiely et al. | 549/262 |
| 4,729,978 A | | 3/1988 | Sawicki | 502/174 |
| 4,786,756 A | | 11/1988 | Paparizos et al. | 562/599 |
| 4,975,537 A | * | 12/1990 | Aristoff et al. | |
| 5,068,399 A | | 11/1991 | Naito et al. | 560/212 |
| 5,250,729 A | | 10/1993 | Abe et al. | 562/599 |
| 5,252,473 A | | 10/1993 | Walkup et al. | 435/135 |
| 5,679,832 A | | 10/1997 | Stephens | 560/212 |

FOREIGN PATENT DOCUMENTS

| WO | US 01/31570 | 10/2001 |
|---|---|---|

OTHER PUBLICATIONS

Storey et al, New Epoxy–Terminated Oligoesters: Precursore to Totally Bio degradable Networks, 1993, Journal of Polymer Science, Part A: Polymer Chemistry, 31(7), pp. 1825–1838.*

Burns et al Journal of the Chemical Society 1935, p. 400–406.*

Wurtz, A. et al., "Memoire sur L'Acide Lactique" (Report on Lactic Acid), Annals of Chemistry and Physics, 3rd series, 1861, pp. 101–124 (includes translation).

* cited by examiner

Primary Examiner—Deborah D. Carr
Assistant Examiner—Paul A. Zucker
(74) Attorney, Agent, or Firm—Wells St. John P.S.

(57) ABSTRACT

The present invention provides compounds having the formula:

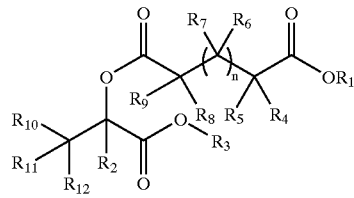

wherein: n is 0 or 1; $R_4$ through $R_{12}$ are independently selected from hydrogen, $C_1$ to $C_{10}$ alkyl, $C_6$ to $C_{10}$ aryl, $C_1$ to $C_{10}$ alkoxy, $C_1$ to $C_{10}$ aryloxy, $C_1$ to $C_{10}$ aralkyl; and $R_1$ through $R_3$ are hydrogen, $C_1$ to $C_{10}$ alkyl, $C_6$ to $C_{10}$ aryl, or $C_1$ to $C_{10}$ aralkyl. Methods of making and using these compounds are also described. Methods of converting α-hydroxy carboxylic esters and acids to acrylates are also described.

30 Claims, No Drawings

ESTER COMPOUNDS AND THEIR USE IN FORMING ACRYLATES

FIELD OF THE INVENTION

The present invention relates to certain ester compounds described herein, methods of forming these ester compounds and the use of these compounds in dehydration reactions to form unsaturated compounds.

BACKGROUND OF THE INVENTION

Scientists and Engineers have long sought improvements in reactions in which a α or β-hydroxy esters or carboxylic acids are dehydrated to the corresponding acrylates. In early work, Burns et al. in J. Chem. Soc., p400–406 (1935) reported the reaction of ethyl lactate and methyl hydrogen phthalate with a sulfuric acid catalyst in benzene, with removal of water in an azeotrope with benzene, to yield methyl α-carboxyethyl phthalate. The methyl α-carboxyethyl phthalate was pyrolyzed to phthalic anhydride and a 41% yield of crude ethyl acrylate.

In other work, Völker et al. (in U.S. Pat. No. 3,487,101, issued December 1969) described several reactions in which α-hydroxy isobutyric acid was dehydrated to methacrylic acid. In example 1, α-hydroxy isobutyric acid was added dropwise to a heated mixture containing phthalic anhydride, dimethylphthalate, caustic soda, and pyrocatechol and hydroquinone as inhibitors. 95.6% of the α-hydroxy isobulyric acid was converted to 90% methacrylic acid and 10% methacrylic acid ester. A similar reaction run without the caustic soda, Example 3, produced a yield of 63%. A reaction similar to Example 1, except where all the reactants were added to a single pot (no slow addition) gave a yield of 71%. While it is unknown whether the Völker method can work to dehydrate secondary α-hydroxyls, since it is well-known that secondary hydroxyls are less labile than tertiary hydroxyls, it might be expected that dehydration of the secondary hydroxyl would not proceed, or perhaps proceed only under very harsh reaction conditions that would favor side reactions. See, for example, March, Advanced Organic Chemistry, Third Ed. p522, which states that "because of the electron-releasing inductive effect of alkyl groups, stability and hence rate of formation of the simple alkyl cation follows the sequence 3°>2°>1°, and Burns et al., "just as tertiary carbinols undergo pyrolytic dehydration more readily, in general, than primary and secondary, so it has been found that their acetates undergo pyrolysis at relatively low temperatures."

Other workers, such as Walkup et al., DeColibus et al., Sawicki, Paprizos et al., and Naito et al. have described methods of dehydrating an alkyl lactate ester or acid to yield the corresponding alkyl acrylate by heating over a catalyst. Walkup et al., in U.S. Pat. No. 5,252,473, described the dehydration of a lactic acid ester to an acrylic acid ester over a catalyst of partially calcined calcium sulfate (see col. 9, line 57 through col. 10, line 56). A long list of other dehydration catalysts that were tested and reported to be inferior is listed by Walkup et al. at col. 11, lines 39–60. DeColibus et al., in U.S. Pat. No. 4,529,816, described a process in which methyl 2-hydroxy-2-methyl propionate is dehydrated in the presence of sulfuric acid to form methyl methacrylate. Sawicki, in U.S. Pat. No. 4,729,978, disclosed a process of selectively converting lactic acid to acrylic acid by dehydrating at about 200 to 400° C. over a phosphate catalyst. Paprizos et al., in U.S. Pat. No. 4,786,756, disclosed a process of converting lactic acid or ammonium lactate to acrylic acid by contacting a mixture of the lactic acid or ammonium lactate and water with aluminum phosphate that has been treated with an inorganic base. Naito et al., in U.S. Pat. No. 5,068,399, described a process in which methyl α-hydroxyisobutyrate in methanol is contacted with a modified molecular sieve aluminosilicate catalyst to yield methyl methacrylate (see Example 1).

Abe et al., in U.S. Pat. No. 5,250,729, described a process similar to Naito et al. except that Abe et al. suggest the substitution of $C_1$–$C_5$ alkoxy groups on the position α or β the ester group having the same alkoxy moiety. These reactions are shown below:

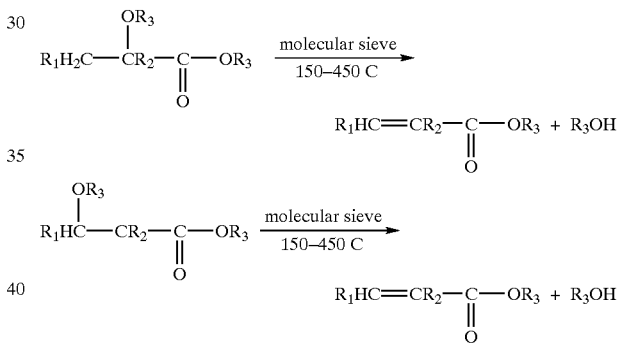

where $R_1$ and $R_2$ represent H or a $C_1$–$C_3$ alkyl and $R_3$ represents a $C_1$–C5 alkyl. In Example 3, Abe et al. disclose a process in which methyl α-methoxyisobutyrate in methanol is contacted with a molecular sieve aluminosilicate catalyst to yield methyl methacrylate.

Stephens in U.S. Pat. No. 5,679,832 disclose a process of making an α,β-unsaturated-β-trifluoromethyl carboxylate from the β-hydroxy alkyl ester. This process is illustrated below:

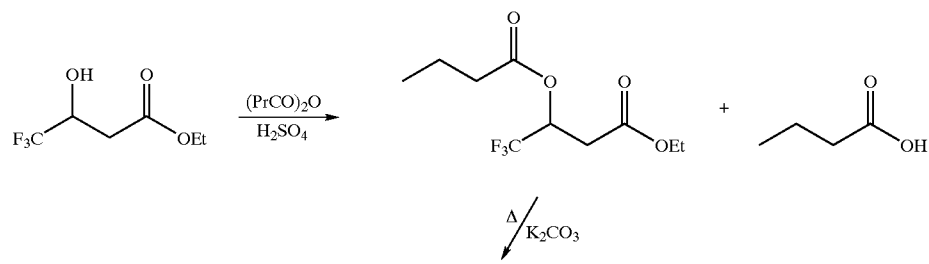

-continued

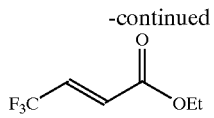

A distillate was collected at 145–160° C. that was found to be 93 wt % ethyl (E)-4,4,4-trifluorobut-2-enoate (87% yield) and 7 wt % butyric acid (see Example 3). In Example 1, ethyl 3-acetyloxy-4,4,4-trifluorobutanoate was heated in the presence of $K_2CO_3$ and a distillate was collected at a bath temperature of 140–180° C. Stephen reported the distillate as a 60:40 molar mixture of ethyl (E)-4,4,4-trifluorobut-2-enoate (87% yield) and acetic acid.

Kiely et al. in U.S. Pat. No. 4,617,405 disclosed a process of (a) reacting an acid anhydride and the beta-hydroxy carbonyl compound in the presence of an acid catalyst to form an ester; (b) reacting the ester in the presence of a base catalyst to form an α,β-unsaturated carbonyl compound and a carboxylic acid, and (c) separating the α,β-unsaturated carbonyl compound and the carboxylic acid.

Despite these and many other efforts, there remains a need for improved methods for producing acrylates from α-hydroxy esters or α-hydroxy carboxylic acids. There is a particular need for new methods for dehydrating α-hydroxy esters or α-hydroxy carboxylic acids, where the hydroxy moiety is a secondary hydroxy.

SUMMARY OF THE INVENTION

The present invention provides compositions comprising a compound having the formula (III):

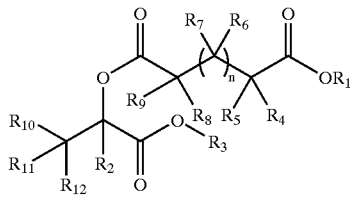

wherein: n is 0 or 1; $R_4$ through $R_{12}$ are independently selected from hydrogen, $C_1$ to $C_{10}$ alkyl, $C_6$ to $C_{10}$ aryl, $C_1$ to $C_{10}$ alkoxy, $C_1$ to $C_{10}$ aryloxy, $C_1$ to $C_{10}$ aralkyl; and $R_1$ through $R_3$ are hydrogen, $C_1$ to $C_{10}$ alkyl, $C_6$ to $C_{10}$ aryl, or $C_1$ to $C_{10}$ aralkyl. In preferred embodiments, when $R_1$ is hydrogen, $R_2$ is hydrogen. In some preferred embodiments, where $R_1$ is not hydrogen, $R_1$ is the same as $R_3$ and the concentration of the compound of formula III is more than twice the concentration of analogous compounds where $R_1$ is not the same as $R_3$; by "analogous compounds" it is meant compounds that have the same structure as the compound of formula III except that $R_1$ and $R_3$ are not equal ($R_1 \neq R_3$), and $R_1$ is not H, and $R_3$ is not H. In some other preferred embodiments, the compound of formula III is present in a concentration greater than the concentration of anhydride and greater than the concentration of the compounds of formula I.

The invention also provides methods of making compounds having the structure of formula III. Preferably, this method comprises reacting a compound having formula I:

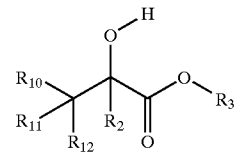

with a compound having formula II:

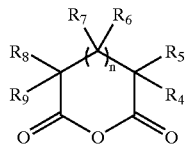

wherein the R groups are defined as above.

The invention also includes compositions made by the reaction of I and II.

The invention also provides a method of making acrylates (and methods of using compounds of formula III) wherein a compound of formula III is heated to yield an acrylate and an anhydride. Preferably, the method of making an acrylate is a two step process in which a compound of formula I is reacted with a compound of formula II under a first set of conditions, then the compound of formula III is thermolyzed at a higher temperature to form the acrylate. In preferred embodiments of this two step method, the compound of formula III is isolated from the compounds of formulas I and II before it is decomposed to produce the acrylate.

In the present invention, the term "acrylate" refers to a compound having the C=C—C(O)OR moiety.

Various embodiments of the invention can provide numerous advantages including: few side reactions, high yield, volatile starting materials and products that can be conveniently distilled and recycled, isolable intermediates, initial reactions that do not form water (less deesterification), lower process temperatures, and excellent applicability to large scale processing.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF PREFERRED EMBODIMENTS

In some preferred embodiments of the invention, there are compositions comprising a compound having the formula (III):

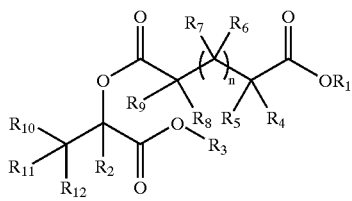

wherein: n is 0 or 1; $R_4$ through $R_{12}$ are independently selected from hydrogen, $C_1$ to $C_{10}$ alkyl, $C_6$ to $C_{10}$ aryl, $C_1$ to $C_{10}$ alkoxy, $C_1$ to $C_{10}$ aryloxy, $C_1$ to $C_{10}$ aralkyl; and $R_1$ through $R_3$ are hydrogen, $C_1$ to $C_{10}$ alkyl, $C_6$ to $C_{10}$ aryl, or $C_1$ to $C_{10}$ aralkyl, provided that when $R_1$ is hydrogen, $R_2$ is hydrogen. When n is 0, $R_6$ and $R_7$ are not present, and there is a two carbon chain connecting the two carbonyl carbons.

Preferably, the composition has essentially no analogous compounds where $R_1$ is not the same as $R_3$, by "essentially no," it is meant that there the concentration of analogous compounds is sufficiently low such that they would have less than a 5% adverse effect on the yield of the desired acrylate formed by the thermolysis of the composition.

The alkyl, aryl and aralkyl, as those terms are used herein, can also contain hetero atoms such as O, N, Si, and S and can have substituents such as halo, hydroxy, phosphate, sulfonate and carboxylate. In some preferred embodiments, the alkyl, aryl and aralkyl are $C_1$ to $C_{10}$ hydrocarbons without hetero atoms. In some preferred embodiments, the R groups are all hydrogen or members of the $C_1$ to $C_6$ alkyls.

While compounds of formula III have been described with reference to $C_1$ to $C_{10}$ alkyl, etc., it will be appreciated by those skilled in the art that the methods described herein can be applied to synthesizing a myriad of other compounds, and further that most of these compounds will thermolyze by analogous routes to produce the corresponding products.

The chain length of the "upper" chain (i.e., the chain in which n is 0 to 1) is selected to facilitate ring closing to form an anhydride. Similarly, $R_4$ through $R_9$ are preferably selected to have low steric bulk so that these groups do not interfere with ring closure.

Some preferred embodiments are comprised of various combinations of the following subsets: n is 0, $R_4$–$R_{12}$ are independently H, methyl, ethyl, propyl, butyl or pentyl, $R_2$ is H, and $R_3$ is H or methyl, ethyl or propyl, $R_2$ and $R_3$ are independently H, methyl, ethyl, propyl, butyl or pentyl, $R_1$ is H, and $R_1$ is methyl, ethyl, propyl, butyl or pentyl.

In some preferred embodiments, $R_1$ is H, methyl, ethyl or propyl; $R_2$ and $R_3$ are both H; n is 0 or 1; $R_4$–$R_{12}$ are H; $R_2$ is H; and $R_3$ is H, methyl, ethyl or propyl. In a particular embodiment, $R_1$ is H, methyl, ethyl or propyl, n is 0, $R_4$–$R_{12}$ are H, $R_2$ is H, and $R_3$ is methyl.

The composition can also be characterized by its properties. In preferred embodiments, the compound of formula III in the composition thermally decomposes to form an equimolar amount of an acrylate and an equimolar amount of an anhydride or its precursor. If desired, products can be distilled off and recycled to the synthesis stage in which I and II are reacted.

Preferred compositions can also be characterized by their purity. In a preferred embodiment, the composition has a molar ratio of the compound of formula III: compound of formula II of at least 0.5, more preferably at least 2, and still more preferably more than 10.

In preferred compounds of formula I, $R_2$ is H. More preferably, the compound of formula I is lactic acid, ethyl lactate, propyl lactate, butyl lactate or other lactate derivative. Most preferably, the compound of formula I is methyl lactate, which results in the best yield of acrylate.

Preferred compounds of formula II are succinic anhydride and glutaric anhydride. Since the compound of formula II can be recovered when the acrylate is formed, relatively expensive compounds can also be selected. If desired, these compounds can be distilled off and recycled to the synthesis stage to again react with compound I.

Another of the advantages of preferred embodiments of the present invention that has not been recognized in the art, is the control of alkyl moieties at $R_1$ and $R_3$ to insure that these moieties are the same and thus prevent undesirable transesterification reactions that can lower yield of acrylate and cause undesirable side reactions.

One of the discoveries of the present invention is that the compounds of formulas I and II can react to form isolable compounds of formula III; and it is especially surprising that the reaction can occur under mild conditions. Preferably, these compounds are reacted at a temperature of about 150° C. or less, more preferably at about 50° C. to about 140° C. Higher temperatures may be used; however, these higher temperatures are unnecessary and can result in lower yields. Dropwise addition is unnecessary and it is believed that dropwise addition does not produce higher yields; thus, in preferred embodiments the reaction of I and II is not carried out in a dropwise fashion. The reaction is preferably conducted in the presence of an acid or base catalyst. It has been found that dimethylaminopyridine is an especially effective catalyst for this reaction. The reaction can be conducted without solvents; however, in other embodiments, a solvent or solvents may be present.

If the reaction is run under sufficiently harsh conditions, the compound of formula III can be converted to an acrylate in a single step including the reaction of compounds I and II. More preferably, a compound of formula III is isolated before it is heated to produce an acrylate. This isolation step leads to fewer impurities in the acrylate final product. The isolation step also offers a significant advantage for large scale applications. For example, the initial reaction of compounds I and II can be carried out in a batch reactor while the compound of formula III can be transferred to a continuous reactor to produce good yields of relatively pure acrylate and an anhydride, or its precursor (for example, monomethylsuccinate is the precursor of succinic anhydride), that is recycled to the batch reactor. Thus, in one preferred method, compounds I and II are reacted in a first reactor and then, in a subsequent step, compound III is transferred to a different reactor. In some preferred embodiments, the composition containing a compound of formula III is separated from catalysts and then thermolyzed in the absence of a catalyst.

Isolating the compound of formula III can be accomplished by methods such as: distillation or extraction, or could be simply carried out by reacting compounds I and II and allowing the product III to accumulate (in a concentration greater than that of I and greater than that of II) before it is thermolyzed. This could be accomplished, for example, by running the reaction of compounds I and II at a first, lower temperature or temperatures (at which the compound of formula III is essentially unreactive), and then thermolyzing compound III at a higher temperature.

The carboxylic acid resulting from the reaction of compounds I and II can be esterified with an alcohol. This esterification reaction can help stabilize the compound and facilitate purification. As a result, it is believed that higher yields of acrylate and/or greater purity can be achieved.

EXAMPLE

Preparation of Succinic Acid 1-Methoxycarbonyl-ethyl Ester Methyl Ester (i)

Methyl lactate (14 mL, 0.147 moles), succinic anhydride (14.76 g, 0.147 moles), and 2 drops of concentrated sulfuric acid were mixed and heated to 70° C. for five hours. An NMR spectrum of a sample of the cooled reaction mixture showed quantitative conversion to succinic acid (ethyl-1-methoxycarbonyl) ester. Methanol (30 mL) and chloroform (20 mL) were added and heated to reflux in a soxhlet extractor containing silica gel in the receiver. The solution was refluxed for three hours, neutralized with $CaCO_3$, filtered, and the volatile solvents removed under vacuum. The isolated yield of (i) was 29.56 g (98.5%).

CLOSURE

While preferred embodiments of the present invention have been shown and described, it will be apparent to those skilled in the art that many changes and modifications may be made without departing from the invention in its broader aspects. The appended claims are therefore intended to include all such changes and modifications as fall within the true spirit and scope of the invention.

We claim:

1. A composition comprising:

a compound having the formula (III):

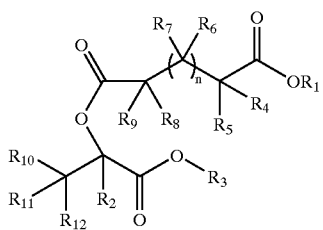

wherein; n is 0 or 1; $P_4$ through $R_{12}$ are independently selected from hydrogen, $C_1$ to $C_{10}$ alkyl, $C_6$ to $C_{10}$ aryl, $C_1$ to $C_{10}$ alkoxy, $C_1$ to $C_{10}$ aryloxy, and $C_1$ to $C_{10}$ aralkyl; $R_2$ is hydrogen, $C_1$ to $C_{10}$ alkyl, $C_6$ to $C_{10}$ aryl, or $C_1$ to $C_{10}$ aralkyl; $R_1$ and $R_3$ are $C_1$ to $C_{10}$ alkyl, $C_6$ to $C_{10}$ aryl, or $C_1$ to $C_{10}$ aralkyl; provided that $R_1 = R_3$; and one or more compounds analogous to formula III, provided that the concentration of the compound of formula III is more than twice the concentration of the analogous compounds; where analogous compounds are defined as compounds having the same structure as formula III except that $R_1$ is not the same as $R_3$.

2. The composition of claim 1 comprising a compound of formula III in which n is 0.

3. The composition of claim 1 comprising a compound of formula III in which $R_1$ and $R_3$ are methyl.

4. The composition of claim 1 made by reacting, at a temperature of about 150° C. or less, a compound of formula I:

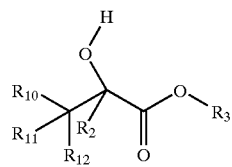

with a compound of formula II:

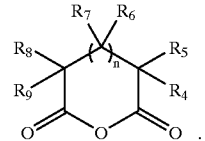

5. The composition of claim 1 comprising a compound of formula III that, after exposure to a temperature above about 200° C., decomposes to an acrylate and an anhydride or its precursor.

6. The composition of claim 4 wherein the composition has a molar ratio of the compound of formula III: compound of formula II of at least 0.5.

7. A composition comprising:

a compound having the formula (III):

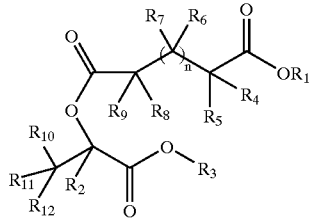

wherein: n is 0 or 1; $R_2$ and $R_4$ through $R_{12}$ are independently selected from hydrogen, $C_1$ to $C_{10}$ alkyl, $C_6$ to $C_{10}$ aryl, $C_1$ to $C_{10}$ alkoxy, $C_1$ to $C_{10}$ aryloxy, and $C_1$ to $C_{10}$ aralkyl; $R_1$ and $R_3$ are $C_1$ to $C_{10}$ alkyl, $C_6$ to $C_{10}$ aryl, or $C_1$ to $C_{10}$ aralkyl; and $R_1 = R_3$; and one or more compounds analogous to formula III; where analogous compounds are defined as compounds having the same structure as formula III except that $R_1$ is not the same as $R_3$; provided that the concentration of the compound of formula III is more than twice the concentration of the analogous compounds; and the compound of formula III being present in a concentration greater than a concentration of any anhydrides present in the composition, and greater than any concentration of compounds of formula I present in the composition, where formula I is:

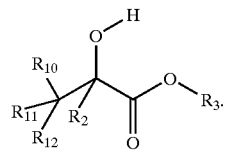

8. The composition of claim 7 wherein $R_2$ is H, $R_1$ and $R_3$ are methyl, $R_4$ is H, $R_6$ and $R_7$ (if present) are H, and $R_8$–$R_{12}$ are H.

9. The composition of claim 8 wherein n is zero.

10. A method of making acrylate comprising the steps of:
isolating a compound having the formula (III):

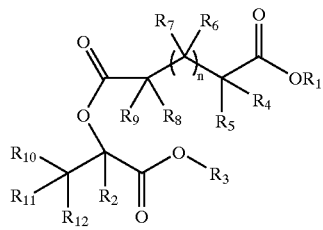

wherein: n is 0 or 1; $R_2$ and $R_4$ through $R_{12}$ are independently selected from hydrogen, $C_1$ to $C_{10}$ alky, $C_6$ to $C_{10}$ aryl, $C_1$ to $C_{10}$ alkoxy, $C_1$ to $C_{10}$ aryloxy, and $C_1$ to $C_{10}$ aralkyl; $R_1$ and $R_3$ are $C_1$ to $C_{10}$ alkyl, $C_6$ to $C_{10}$ aryl, or $C_1$ to $C_{10}$ aralkyl; and $R_1=R_3$; and subsequently heating the compound to produce the acrylate.

11. The method of claim 10 wherein $R_2$ is H.

12. The method of claim 10, wherein $R_1$ and $R_3$ are methyl, and wherein the step of isolating comprises separating the compound of formula III from a catalyst.

13. A method of making a compound comprising:
reacting, at a temperature of about 150° C. or less,
a compound of formula I:

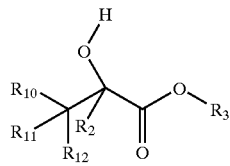

with a compound having formula II:

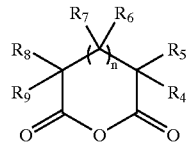

to form a compound having the formula (III):

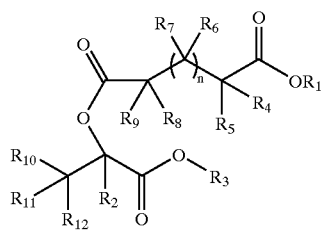

wherein: n is 0 or 1; $R_2$ and $R_4$ through $R_{12}$ are independently selected from hydrogen, $C_1$ to $C_{10}$ alkyl, $C_6$ to $C_{10}$ aryl, $C_1$ to $C_{10}$ alkoxy, $C_1$ to $C_{10}$ aryloxy, and $C_1$ to $C_{10}$ aralkyl; $R_1$ and $R_3$ are $C_1$ to $C_{10}$ alkyl, $C_6$ to $C_{10}$ aryl, or $C_1$ to $C_{10}$ aralkyl; and $R_1=R_3$.

14. A method of making a compound comprising:
reacting, at a temperature of about 150° C. or less,
a compound of formula I:

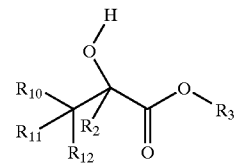

with a compound having formula II:

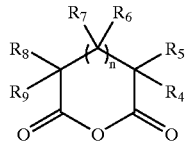

to form a compound having the formula (III):

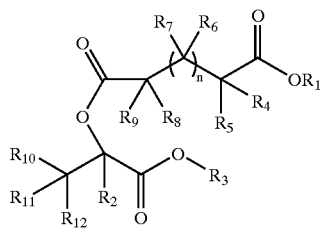

wherein: n is 0 or 1; $R_2$ through $R_{12}$ are independently selected from hydrogen, $C_1$ to $C_{10}$ alkyl, $C_6$ to $C_{10}$ aryl, $C_1$ to $C_{10}$ alkoxy, $C_1$ to $C_{10}$ aryloxy, and $C_1$ to $C_{10}$ aralkyl; $R_1$ is hydrogen, $C_1$ to $C_{10}$ alkyl, $C_6$ to $C_{10}$ aryl, or $C_1$ to $C_{10}$ aralkyl; and simultaneous with or subsequent to the reaction of I and II, a compound of formula III wherein $R_1$ is H is reacted with an alcohol to form a compound of formula III wherein $R_1$ is $C_1$ to $C_{10}$ alkyl, $C_6$ to $C_{10}$ aryl, or $C_1$ to $C_{10}$ aralkyl.

15. The method of claim 13 further comprising isolating the compound of formula III.

16. The method of claim 15 in which $R_2$ is H, $R_1$ and $R_3$ are methyl, $R_4$ is H, $R_6$ and $R_7$ (if present) are H, and $R_8$–$R_{12}$ are H, and further comprising thermolyzing the compound of formula III to form an acrylate.

17. The composition of claim 1 in which $R_1$ is selected from the group consisting of methyl, ethyl, and propyl.

18. The composition of claim 17 in which n is 1, and $R_4$–$R_{12}$=H.

19. The composition of claim 7 in which n=0, $R_1$ and $R_3$ are methyl, and all other R groups are H.

20. The method of claim 13 wherein the compound of formula I is methyl lactate.

21. The method of claim 13 wherein the compound of formula I is reacted with the compound of formula II at a temperature of 50 to 140° C.

22. The method of claim 21 wherein the compound of formula I is reacted with the compound of formula II in the presence of an acid or base catalyst.

23. The method of claim 21 wherein the compound of formula I is reacted with the compound of formula II in the presence of dimethylaminopyridine.

24. The method of claim 10 wherein the compound is heated to form the acrylate in the absence of a catalyst.

25. A compound having the formula

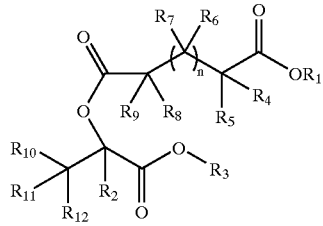

wherein: n is 0 or 1; $R_4$ through $R_{12}$ are independently selected from hydrogen, $C_1$ to $C_{10}$ alkyl, $C_6$ to $C_{10}$ aryl, $C_1$ to $C_{10}$ alkoxy, $C_1$ to $C_{10}$ aryloxy, and $C_1$ to $C_{10}$ aralkyl; $R_2$ is hydrogen, $C_1$ to $C_{10}$ alkyl, $C_6$ to $C_{10}$ aryl, or $C_1$ to $C_{10}$ aralkyl; $R_1$ and $R_3$ are $C_1$ to $C_{10}$ alkyl, $C_6$ to $C_{10}$ aryl, or $C_1$ to $C_{10}$ aralkyl; provided that $R_1$=$R_3$.

26. The compound of claim 25 wherein n is 0.

27. The compound of claim 25 wherein $R_1$ and $R_3$ are methyl.

28. The compound of claim 25 wherein n is 1, $R_1$ and $R_3$ are methyl, $R_4$ is H, and $R_6$–$R_{12}$ are H.

29. The compound of claim 25 wherein $R_2$ is H.

30. The compound of 25 claim wherein n is 0, $R_2$ is H, $R_4$ and $R_6$–$R_{12}$ are H, and $R_1$ and $R_3$ are selected from the group consisting of methyl, ethyl, propyl and butyl.

* * * * *

UNITED STATES PATENT AND TRADEMARK OFFICE
CERTIFICATE OF CORRECTION

PATENT NO. : 6,545,175 B1
DATED : April 8, 2003
INVENTOR(S) : Todd A Werpy et al.

It is certified that error appears in the above-identified patent and that said Letters Patent is hereby corrected as shown below:

Column 2,
Lines 36-38, replace $\underset{\displaystyle\underset{O}{\|}}{R_1HC-CR_2-\overset{\displaystyle OR_3}{C}-OR_3}$ with $\underset{\displaystyle\underset{O}{\|}}{R_1HC-CR_2-\overset{\displaystyle OR_3}{C}-OR_3}$ Column 7,
Line 46, replace "wherein; n is 0 or 1; $P_4$ through $R_{12}$ are independently" with
-- wherein; n is 0 or 1; $R_4$ through $R_{12}$ are independently --

Signed and Sealed this

Twenty-sixth Day of August, 2003

JAMES E. ROGAN
*Director of the United States Patent and Trademark Office*